(12) United States Patent
Sundermeyer et al.

(10) Patent No.: US 10,093,687 B2
(45) Date of Patent: Oct. 9, 2018

(54) METAL N-AMINOGUANIDINATE COMPLEXES FOR USE IN THIN FILM FABRICATION AND CATALYSIS

(71) Applicant: UMICORE AG & CO. KG, Hanau-Wolfgang (DE)

(72) Inventors: Joerg Sundermeyer, Marburg (DE); Katrin Schlechter, Marburg (DE)

(73) Assignee: UMICORE AG & CO. KG, Hanau-Wolfgang (DE)

( * ) Notice: Subject to any disclaimer, the term of this patent is extended or adjusted under 35 U.S.C. 154(b) by 0 days.

(21) Appl. No.: 15/529,390

(22) PCT Filed: Nov. 25, 2015

(86) PCT No.: PCT/EP2015/077691
§ 371 (c)(1),
(2) Date: May 24, 2017

(87) PCT Pub. No.: WO2016/083471
PCT Pub. Date: Jun. 2, 2016

(65) Prior Publication Data
US 2017/0260213 A1 Sep. 14, 2017

(30) Foreign Application Priority Data
Nov. 28, 2014 (EP) .................................... 14195515

(51) Int. Cl.
C07F 5/06 (2006.01)
C07F 5/00 (2006.01)
(Continued)

(52) U.S. Cl.
CPC ............ C07F 5/069 (2013.01); C07C 281/16 (2013.01); C07F 3/003 (2013.01); C07F 3/06 (2013.01);
(Continued)

(58) Field of Classification Search
None
See application file for complete search history.

(56) References Cited

FOREIGN PATENT DOCUMENTS

WO 2009/012341 A2 1/2009
WO 2012/113761 A1 8/2012

OTHER PUBLICATIONS

Koller et al., "Highly Efficient Aluminum-Catalyzed Hydroamination /-hydrazination of Carbodiimides," Organometallics 2010, 29, 5946-5952. (Year: 2010).*
(Continued)

Primary Examiner — Catherine S Branch
(74) Attorney, Agent, or Firm — Smith, Gambrell & Russell, LLP

(57) ABSTRACT

The present patent application relates to new metal complexes having at least one N-aminoguanidinate ligand. The patent application further relates to the preparation of the new metal complexes and also to their use. The new metal complexes are especially suitable as precursors for the preparation of functional layers by means of gas-phase thin-film processes such as CVD, MO-CVD, MOVPE and ALD. Additionally, they are also suitable as catalysts for olefin hydroamination and for olefin polymerization.

formula 1a (Continued)

-continued

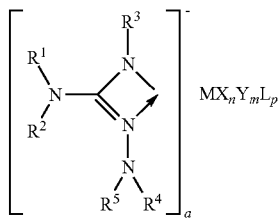

formula 1b

27 Claims, 3 Drawing Sheets

(51) Int. Cl.
| | |
|---|---|
| C07F 5/02 | (2006.01) |
| C23C 16/455 | (2006.01) |
| C07F 3/06 | (2006.01) |
| C07F 3/00 | (2006.01) |
| C08F 10/00 | (2006.01) |
| C23C 16/18 | (2006.01) |
| C07F 15/00 | (2006.01) |
| C07F 15/02 | (2006.01) |
| C07F 5/05 | (2006.01) |
| C23C 16/30 | (2006.01) |
| C07C 281/16 | (2006.01) |

(52) U.S. Cl.
CPC .............. *C07F 5/003* (2013.01); *C07F 5/022* (2013.01); *C07F 5/027* (2013.01); *C07F 5/05* (2013.01); *C07F 5/065* (2013.01); *C07F 15/0066* (2013.01); *C07F 15/025* (2013.01); *C08F 10/00* (2013.01); *C23C 16/18* (2013.01); *C23C 16/30* (2013.01); *C23C 16/45553* (2013.01)

(56) References Cited

OTHER PUBLICATIONS

W.L.F. Armarego, et al. Purification of laboratory chemicals, 7th edition, Elsevier, Burlington, 2012. pp. 29-33 and 52.
W.L.F. Armarego, et al. Purification of laboratory chemicals, 5th edition, Elsevier, Burlington, 2003. pp. 25-29 and 43.
Santra et al. Coupling of Arylamines with Coordinated Arylazopyrimidines in Palladium(II) Complexes. European Journal of Inorganic Chemistry, 2002, pp. 1124-1131.
Pratihar et al. The C—N coupling reaction of pendant naphthyl group of palladium(II) complexes of 1-alkyl-2-(naphthyl-b-azo)imidazoles. Structural characterization, spectral and redox properties, and correlation with DFT computed data. Inorganica Chimica Acta, 2010, 363, pp. 831-840.
Åhman, J, et al. An Efficient Preparation of Potassium Bis (Trimethylsilyl) Amide (KHMDS). Synthetic Communications. 1995. vol. 25, Issue 15, pp. 2301-2303.
Vilkas, M. et al, A Convenient Laboratory Preparation of N,N-Dimethyl-dichloro-methylene-iminium Chloride (Phosgene-iminium chloride). Synthetic Communications. 1990, vol. 20, Issue 18, pp. 2769-2773.
Savelieva, Z. A., et al. Coordinated diammoguanidinium(1+) ion in the crystal structure of the [Cu(CH8N5)C13] complex. Journal of Structural Chemistry. 1995. vol. 36, Issue 5, pp. 855-859.
International Search Report dated Jan. 22, 2016 for International Application No. PCT/EP2015/077691 (5 pages).
Written Opinion of the International Searching Authority dated Jan. 22, 2016 for International Application No. PCT/EP2015/077691 (6 pages).
International Preliminary Report on Patentability dated May 30, 2017 for International Application No. PCT/EP2015/077691 (7 pages).

* cited by examiner

METAL N-AMINOGUANIDINATE COMPLEXES FOR USE IN THIN FILM FABRICATION AND CATALYSIS

The present patent application relates to new metal complexes having at least one N-aminoguanidinate ligand and to the preparation of the metal complexes and their use.

The new metal complexes are preferably used as precursors in thin-film processes. In particular, the new metal complexes are used as precursors for producing functional layers by means of gas-phase deposition processes such as CVD (chemical vapour deposition), MO-CVD (metal organic chemical vapour deposition) and ALD (atomic layer deposition). Additionally, the complexes are preferably also suitable as catalysts for olefin hydroamination and for olefin polymerization.

Chemical gas-phase deposition (CVD) is a gas-phase reaction (usually on or in the vicinity of the substrate surface). In such reactions, the reaction gases are passed simultaneously into the reaction chamber with the substrate to be coated. The gases, which are usually pre-heated, are activated thermally by the heated substrate, and react with one another. In the course of this reaction, the desired material is deposited and chemically bound (chemisorption).

In addition to countless CVD variants, which differ in operating pressure and other operational parameters, there also exist certain coating processes which represent CVD processes modified to a greater or lesser extent:

In the process known as plasma polymerization, gaseous monomers excited by a plasma form a highly cross-linked layer on a substrate.

Atomic layer deposition (ALD) is a highly modified CVD process, in which the reaction or sorption on the surface stops automatically after the complete covering of the surface. This self-limiting reaction is run in a plurality of cycles (with rinsing steps in between them), thereby achieving very good aspect ratios (length/thickness ratios) and exact layer thicknesses.

The class of N-aminoguanidinate ligands is based on a guanidine framework, where at least one of the three guanidine nitrogen atoms is substituted with an $NR_2$ group by direct N—N bonding. In the coordinated state, the ligands are bidentate, with two N atoms being coordinated to the metal (M) and a five-membered ring of sequence M—N—N—C—N— being formed. In the coordinated state, the ligands preferably have a single negative charge. Homoleptic and heteroleptic metal complexes may be formed.

Metal complexes containing bidentate N-aminoguanidine ligands are known from the literature.

Santra et al., *Eur. J. Inorg. Chem.*, 2002, 1124-1131, describe the preparation of palladium complexes of 2-(Arylazo)pyrimidines (aapm) and their coupling reaction with arylamines. The described $Pd(aapm)Cl_2$ complexes are of formula A,

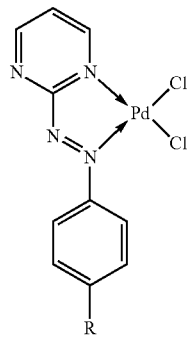

formula A wherein R is H, $CH_3$ or Cl.

The complexes contain a five-membered ring of the sequence Pd—N—N—C—N—. However, the nitrogen atom that is bound to the guanidine core structure is substituted with a bulky aryl group. Thereby, the volatility of the complexes is strongly reduced. Furthermore, two of the guanidine nitrogen atoms are interconnected by a $C_3$-unit so that a six-membered ring is formed within the ligand including the guanidine core. This results in decreased flexibility as well as impaired and less reproducible decomposition.

Pratihar et al., *Inorganica Chimica Acta*, 2010, 363, 831-840, describe the coupling reaction of Dichloro-(1-alkyl-2-(naphtyl-β-azo)imidazole)palladium(II) complexes (Pd(β-NaiR)$Cl_2$) with arylamines. The described complexes are shown in formula B,

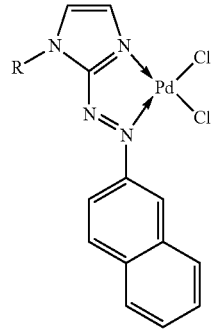

formula B wherein R is $CH_3$, $CH_2CH_3$ or $CH_2Ph$.

The described complexes contain a five-membered ring of the sequence Pd—N—N—C—N—. However, the nitrogen atom that is bound to the guanidine core structure is substituted with a bulky aryl group. Thereby, the volatility of the complexes is strongly reduced. Furthermore, two of the guanidine nitrogen atoms are interconnected by a $C_2$-unit so that a five-membered ring is formed within the ligand including the guanidine core. This results in decreased flexibility as well as impaired and less reproducible decomposition.

WO 2012/113761 discloses N-aminoamidinate complexes and their uses. However, no lanthanide complexes can be obtained from these ligands and the complexes obtained were difficult to purify due to their low melting points that made recrystallization more difficult.

In the fabrication of semiconductor components (processors, memory chips, sensor chips etc.) it is usual for the deposition of metallic, oxidic and nitridic layers to employ CVD, MO-CVD and ALD processes. These processes have now acquired great significance in semiconductor technology and microelectronics.

In these processes, the substrate is coated at the interface between substrate and gas phase by vaporization and heating of a suitable precursor compound above the decomposition point, often in the presence of a reactive gas (such as hydrogen, ammonia or 1,1-dimethylhydrazine). Processes of these kinds are used, for example, to generate layers of GaN, InN, TaN, TiN or $Si_3N_4$.

It is also possible to deposit metallic layers (for example Pd, Ru or Co). In order to be suitable for use in CVD, MOVPE and ALD, the appropriate ligands and metal complexes ought to possess a molecular construction (and should ideally be present as monomer), possess a low molar mass, and have a high volatility and a low decomposition point at temperatures above the storage temperature.

Furthermore, they ought to be thermally stable at room temperature, so that there is no decomposition prior to the deposition process. In addition, the compounds should possess a uniform, reproducible decomposition mechanism, and should have suitable predetermined breakage points for the fragmentation in the molecule. Lastly, with a defined precursor compound under identical CVD conditions, it should always be possible to deposit the same layer with consistent quality.

Suitable ligands for such precursor compounds ought to provide good steric shielding of the metal centre, be electron-rich, and should electronically satisfy the metal centre, thereby lowering the Lewis acidity and inhibiting the aggregation of the compounds into coordination polymers of low volatility. During the deposition, furthermore, a reduction of the metal centre is frequently necessary. Ligands which contain a high proportion of hydrazine structural units, such as the ligands of the present patent application, carry reduction equivalents with them per se.

Preferably, ligands of precursor compounds for the fabrication of semiconductor components have high nitrogen content. On the one hand, high nitrogen content in the ligand increases the incorporation rate of nitrogen into the semiconductor elements. On the other hand, high nitrogen content in the ligand renders the use of reactive gases obsolete as they are intramolecularly contained in the ligand and are thus produced upon ligand decomposition.

The existing metal complexes such as those with N-aminoguanidine ligands have disadvantages. They possess, for instance, bulky aryl groups bound to the amino group, with which the guanidine core is substituted. This results in a high molar mass and thus in low volatility. Furthermore, two of the guanidine nitrogen atoms are part of an intra-ligand ring structure leading to decreased conformational flexibility of the ligand. The use of these aminoguanidinate complexes as precursors in thin-film deposition processes may therefore lead to disadvantages with respect to reproducibility, layer quality, deposition rate and yield.

It is, therefore, an object to provide improved metal complexes. These metal complexes should be suitable for use in thin-film deposition processes. They should have a low molecular mass and a high volatility. They should also be stable for storage. They should be decomposable in a defined and reproducible manner. The metal complexes should also be suitable to be used as catalysts for olefin hydroamination and for olefin polymerization.

The object is achieved by the new N-aminoguanidinate metal complexes as claimed in the present claims. These new metal complexes are characterized in that they contain at least one N-aminoguanidinate ligand. These metal complexes have a low molecular mass and an advantageously high volatility. They are also characterized by a high nitrogen content that is higher than e.g. in N-aminoamidinate complexes.

A field of application of the title compounds, in particular those, that combine group 13 metals (B, Al, Ga, In) incorporating metal alkyl or hydride functionalities and N-aminoguanidinate ligands is the metal organic vapour phase epitaxy (MOVPE) growth of dilute nitride III-V semiconductor materials such as $GaAs_{1-x}N_x$ or $InP_{1-x}N_x$. The goal is to lower the high activation barrier, the high deposition temperature and the large excess of ammonia or other nitrogen sources typically needed during casting of substantial amounts of N atoms via MOVPE into the GaAs and InP growth process, and into meta-stable III-V semiconductor materials in general. The higher nitrogen content in comparison to corresponding N-aminoamidinate complexes is, next to direct metal-nitrogen bonds, may result in a higher rate of nitrogen implantation into the deposited layer and different ligand decay paths compared to N-aminoamidinates. As one or two hydrazine units with particular weak N—N bonds are bound to the metal, these novel precursors are especially suitable to be used in thin-film deposition processes. The present patent application thus also relates to the use of the metal complexes as precursors in thin-film processes, in particular wherein the thin-film process is selected from the group of CVD processes such as MO-CVD processes and ALD processes.

Furthermore, the new metal complexes are also suitable as catalysts for olefin hydroamination and for olefin polymerization. The metal complexes enable an increased catalytic activity in olefin hydroamination and polymerization reactions due to their ligands, which are advantageously electron-rich. The present patent application thus also relates to the use of the metal complexes as catalysts for olefin hydroamination or olefin polymerization.

The present patent application relates to metal complexes having at least one N-aminoguanidinate ligand, wherein these metal complexes are of formula 1a or 1b formula 1a

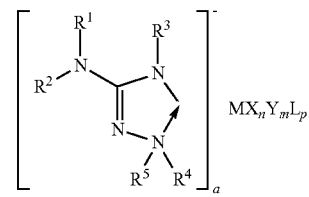

formula 1b

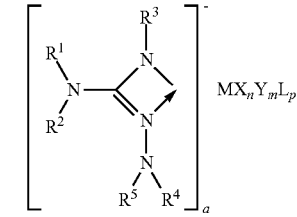

wherein

M is a metal selected from the groups 1 to 15 of the periodic table of elements (PTE), lanthanides or actinides;

$R^1$ is hydrogen, a cyclic, linear or branched alkyl radical having up to 5 carbon atoms, $NH_2$, $NH(CH_3)$, $N(CH_3)_2$, $N(C_2H_5)_2$ or N-pyrrolidinyl, or $R^1$ and $R^2$ together with the nitrogen atom they are bonded to form a pyrrolidinyl ring;

$R^2$ is hydrogen, a cyclic, linear or branched alkyl radical having up to 5 carbon atoms, or $R^2$ and $R^1$ together with the nitrogen atom they are bonded to form a pyrrolidinyl ring;

$R^3$ is hydrogen or a cyclic, linear or branched alkyl radical having up to 8 carbon atoms, $NH_2$, $NH(CH_3)$, $N(CH_3)_2$, $N(C_2H_5)_2$ or N-pyrrolidinyl or a $SiMe_3$ group;

$R^4$ and $R^5$ independently of one another are hydrogen or a linear or branched alkyl radical having up to 4 carbon atoms, or $R^4$ and $R^5$ together with the nitrogen atom they are bonded to form a pyrrolidinyl ring;

X is a monoanionic co-ligand selected from the hydride anion ($H^-$), from the group of the halides, from the group of the cyclic, linear or branched alkylides having up to 8 carbon atoms, from the group of substituted or unsubstituted arylides and heteroarylides having up to 10 C atoms, from the group of alkoxylato ligands, from the group of alkylthiolato or alkylselenolato ligands or from the group of secondary amido ligands;

Y is a dianionic coligand selected from the oxido group $[O]^{2-}$, the sulfido group $[S]^{2-}$ or the imido group $[NR^6]^{2-}$, where $R^6$ is a cyclic, branched or linear alkyl having up to 8 carbon atoms or is a substituted or unsubstituted aryl having up to 20 carbon atoms;

L is a neutral 2-electron donor ligand;

a is an integer between 1 and 4; and n, m, and p each independently of one another are 0, 1, 2, 3 or 4.

In the complexes of the present patent application the metal atom may be present in the formal oxidation states from +1 to +6. Suitable oxidation states are in particular selected from +1, +2 and +3. The at least one N-aminoguanidinate ligand carries a negative charge and is therefore in monoanionic form. Hence, the ligand is electron-rich and electronically satisfies the metal centre. Thereby, the ligand advantageously lowers the Lewis acidity and inhibits aggregation into coordination polymers of low volatility. This has proven to be advantageously for thin-film deposition processes.

The central atom M used in the complexes is a metal from groups 1 to 15 of the periodic table of elements (PTE). This encompasses the metals of the s block (groups 1 and 2, i.e. alkali metals and alkaline earth metals), the metals of the p block (groups 13, 14 and 15) and the metals of the d block (transition metals from groups 3 to 12) of the PTE. This definition also encompasses all metals within the periods of the PTE, hence including the precious metals. The central atom M may also be selected from the group of lanthanides or actinides. Lanthanides are known to be the metals lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb) and lutetium (Lu). Actinides are known to be the metals actinium (Ac), thorium (Th), protactinium (Pa), uranium (U), neptunium (Np), plutonium (Pu), americium (Am), curium (Cm), berkelium (Bk), californium (Cf), einsteinium (Es), fermium (Fm), mendelevium (Md), nobelium (No), lawrencium (Lr).

Preferably, M is selected from the group of boron (B), aluminium (Al), gallium (Ga), indium (In), silicon (Si), germanium (Ge), tin (Sn), arsenic (As), antimony (Sb), titanium (Ti), zirconium (Zr), hafnium (Hf), chromium (Cr), manganese (Mn), iron (Fe), cobalt (Co), nickel (Ni), copper (Cu), zinc (Zn), ruthenium (Ru), rhodium (Rh), palladium (Pd) and platinum (Pt). More preferably, M is selected from the group of boron (B), aluminium (Al), gallium (Ga), indium (In), germanium (Ge), tin (Sn), antimony (Sb), titanium (Ti), zirconium (Zr), cobalt (Co), nickel (Ni), copper (Cu), zinc (Zn), ruthenium (Ru), rhodium (Rh), palladium (Pd) and platinum (Pt). Even more preferably, M is selected from the group of boron (B), aluminium (Al), gallium (Ga), indium (In) and palladium (Pd).

In a specific embodiment, the complex has the formula 1a and the central atom M used in the complexes is a metal from groups 1 to 15 of the periodic table of elements (PTE). Specifically, the central atom M is selected from the metals of the s block (groups 1 and 2, i.e. alkali metals and alkaline earth metals), the metals of the p block (groups 13, 14 and 15) and the metals of the d block (transition metals from groups 3 to 12) of the PTE. More specifically, M is selected from the group of boron (B), aluminium (Al), gallium (Ga), indium (In), silicon (Si), germanium (Ge), tin (Sn), arsenic (As), antimony (Sb), titanium (Ti), zirconium (Zr), hafnium (Hf), chromium (Cr), manganese (Mn), iron (Fe), cobalt (Co), nickel (Ni), copper (Cu), zinc (Zn), ruthenium (Ru), rhodium (Rh), palladium (Pd) and platinum (Pt). Even more specifically, M is selected from the group of boron (B), aluminium (Al), gallium (Ga), indium (In), germanium (Ge), tin (Sn), antimony (Sb), titanium (Ti), zirconium (Zr), cobalt (Co), nickel (Ni), copper (Cu), zinc (Zn), ruthenium (Ru), rhodium (Rh), palladium (Pd) and platinum (Pt). Most specifically, M is selected from the group of boron (B), aluminium (Al), gallium (Ga), indium (In) and palladium (Pd). $R^1$ to $R^5$, X, Y, L, a, n, m, p are defined as mentioned above, or as further defined below, respectively.

In another specific embodiment, the complex has the formula 1b and M is selected from the group of lanthanides or actinides. More specifically, M is selected from the group of lanthanum (La), cerium (Ce), praseodymium (Pr), neodymium (Nd), samarium (Sm), europium (Eu), gadolinium (Gd), terbium (Tb), dysprosium (Dy), holmium (Ho), erbium (Er), thulium (Tm), ytterbium (Yb), lutetium (Lu), actinium (Ac), thorium (Th), uranium (U), neptunium (Np), plutonium (Pu). Even more specifically, M is selected from the group of lanthanum (La), cerium (Ce), praseodymium (Pr), neodymium (Nd), samarium (Sm), ytterbium (Yb). $R^1$ to $R^5$, X, Y, L, a, n, m, p are defined as mentioned above, or as further defined below, respectively.

Preferably, $R^1$ is hydrogen or a cyclic, linear or branched alkyl radical having up to 5 carbon atoms. $R^1$ may also be selected from $NH_2$, $NH(CH_3)$, $N(CH_3)_2$, $N(C_2H_5)_2$ or N-pyrrolidinyl. In case the number of carbon atoms in $R^1$ is too high, the resulting metal complexes fail to provide the required high volatility. More preferably, $R^1$ is hydrogen or a linear or branched alkyl radical having up to 4 carbon atoms, or $R^1$ and $R^2$, together with the nitrogen atom they are bonded to, form a pyrrolidinyl ring. More preferably, $R^1$ is hydrogen or a linear or branched alkyl radical having up to 3 carbon atoms. More preferably, $R^1$ is a linear alkyl radical having up to 3 carbon atoms. Even more preferably, $R^1$ is $CH_3$.

Preferably, $R^2$ is hydrogen or a cyclic, linear or branched alkyl radical having up to 5 carbon atoms. In case the number of carbon atoms in $R^2$ is too high, the resulting metal complexes fail to provide the required high volatility. More preferably, $R^2$ is a linear or branched alkyl radical having up to 4 carbon atoms, or $R^2$ and $R^1$, together with the nitrogen atom they are bonded to, form a pyrrolidinyl ring. More preferably, $R^2$ is a linear or branched alkyl radical having up to 3 carbon atoms. More preferably, $R^2$ is a linear alkyl radical having up to 3 carbon atoms. Even more preferably, $R^2$ is $CH_3$.

In especially preferred embodiments $R^1$ and $R^2$ are both linear alkyl radicals having up to 3 carbon atoms, most preferably $R^1$ and $R^2$ are both $CH_3$.

Preferably, $R^3$ is hydrogen or a cyclic, linear or branched alkyl radical having up to 5 carbon atoms, $NH_2$, $NH(CH_3)$, $N(CH_3)_2$, $N(C_2H_5)_2$ or N-pyrrolidinyl. More preferably, $R^3$ is hydrogen, $CH_3$, $C_2H_5$, $NH_2$, $N(CH_3)_2$ or $N(C_2H_5)_2$. Even more preferably $R^3$ is $CH_3$, $C_2H_5$, $N(CH_3)_2$ or $N(C_2H_5)_2$. Most preferably, $R^3$ is $CH_3$, $C_2H_5$ or $N(CH_3)_2$. Especially preferably, $R^3$ is $CH_3$ or $N(CH_3)_2$.

Preferably, $R^4$ and $R^5$ are independently of one another hydrogen or a linear or branched alkyl radical having up to 3 carbon atoms or they form, together with the nitrogen atom they are bonded to, a pyrrolidinyl ring. Preferably, $R^4$ and $R^5$ are independently of one another hydrogen, $CH_3$ or $C_2H_5$. More preferably, $R^4$ and $R^5$ are independently of one another $CH_3$ or $C_2H_5$. Even more preferably, both $R^4$ and $R^5$ are $CH_3$.

Preferably, X is selected from the hydride anion ($H^-$), methylide ($CH_3^-$), ethylide ($C_2H_5^-$), isopropylide (iso-$C_3H_7^-$), tert-butylide (tert-$C_4H_9^-$), the phenylide anion ($C_6H_5^-$), the ortho-, meta-, orpara-tolylide anion [$C_6H_4(CH_3)$]$^-$, the thiophen-2-ylide anion ($C_4H_3S^-$), methylato ($MeO^-$), ethylato ($EtO^-$), tert-butylato (tert-$BuO^-$), $MeS^-$, $MeSe^-$, (tert-Bu)$S^-$, (tert-Bu)$Se^-$, dimethylamido ($NMe_2^-$), diethylamido ($NEt_2^-$), methylethylamido ($NMeEt^-$), N-pyrrolidido [$NC_4H_8$]$^-$, chloride ($Cl^-$) or bromide ($Br^-$). More preferably, X is selected from the hydride anion ($H^-$), methylide ($CH_3^-$), ethylide ($C_2H_5^-$), the phenylide anion ($C_6H_5^-$), the ortho-, meta-, or para-tolylide anion [$C_6H_4(CH_3)$]$^-$, methylato ($MeO^-$), ethylato ($EtO^-$), $MeS^-$, $MeSe^-$, dimethylamido ($NMe_2^-$), diethylamido ($NEt_2^-$), methylethylamido ($NMeEt^-$), chloride ($Cl^-$) or bromide ($Br^-$). Even more preferably, X is selected from the hydride anion ($H^-$), methylide ($CH_3^-$), ethylide ($C_2H_5^-$), the phenylide anion ($C_6H_5^-$), the ortho-, meta-, or para-tolylide anion [$C_6H_4(CH_3)$]$^-$, methylato ($MeO^-$), $MeS^-$, dimethylamido ($NMe_2^-$), diethylamido ($NEt_2^-$) or chloride ($Cl^-$). Even more preferably, X is selected from the hydride anion ($H^-$), methylide ($CH_3^-$), ethylide ($C_2H_5^-$) or isopropylide (iso-$C_3H_7^-$). Even more preferably, X is selected from the hydride anion ($H^-$) or methylide ($CH_3^-$).

Preferably, Y is selected from the oxido group [O]$^{2-}$ or the imido group [$NR^6$]$^{2-}$, where $R^6$ is a cyclic, branched or linear alkyl having up to 6 C atoms or is a substituted or unsubstituted aryl having up to 12 C atoms. More preferably, Y is selected from the oxido group [O]$^{2-}$, or the imido group [$NR^6$]$^{2-}$, where $R^6$ is a branched or linear alkyl having up to 5 C atoms or is a substituted or unsubstituted aryl having up to 8 C atoms. Even more preferably, Y is the imido group [$NR^6$]$^{2-}$, where $R^6$ is a linear or branched alkyl having up to 4 C atoms, such as [$NCH_3$]$^{2-}$, [$NC_2H_5$]$^{2-}$, [N-propyl]$^{2-}$, [N-isopropyl]$^{2-}$, [N-butyl]$^{2-}$, [N-isobutyl]$^{2-}$, [$NC_2H_5$]$^{2-}$, [N$^t$Bu]$^{2-}$. Even more preferably, Y is [N$^t$Bu]$^{2-}$.

Preferably, L is selected from pyridine, dioxane, $NH_3$, THF, CO, an alkylphosphine or an arylphosphine. More preferably, L is selected from pyridine, $NH_3$, CO, $PMe_3$, $PCy_3$ or $PPh_3$. Even more preferably, L is selected from pyridine, $NH_3$ or CO.

In a specific embodiment, the metal complexes have the following formula 2

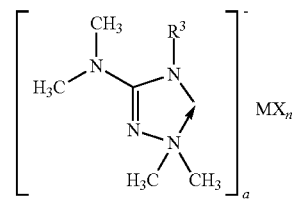

formula 2 wherein
M is B, Al, Ga, In, Zn, Fe or Pd;
$R^3$ is $CH_3$ or $N(CH_3)_2$;
X is the hydride anion ($H^-$) or methylide ($CH_3^-$);
a is 1 or 2; and
n is 0, 1 or 2.

In another specific embodiment, the metal complexes have the following formula 3

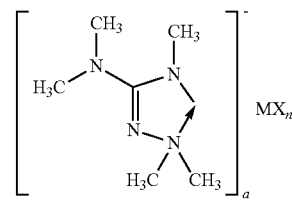

formula 3 wherein
M is B, Al, Ga, In, Zn, Fe or Pd,
X is the hydride anion ($H^-$) or methylide ($CH_3^-$),
a is 1 or 2 and
n is 0, 1 or 2.

In these specific metal complexes the at least one N-aminoguanidinate-ligand is N-dimethylamino-N',N"-trimethylguanidinate (datg).

In another specific embodiment, the metal complexes have the formula 3, wherein M is B, Al, Ga, In or Pd, X is a hydride anion ($H^-$) or methylide anion ($CH_3^-$), a is 1 or 2 and n is 0, 1 or 2. In these specific metal complexes of formula 3, the at least one N-aminoguanidinate-ligand is particularly an N-dimethylamino-N',N"-trimethylguanidinate (datg).

In further specific embodiments, the metal complexes have the following formula 4

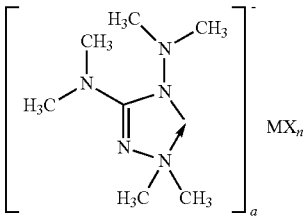

formula 4 wherein
M is B, Al, Ga, In, Zn, Fe or Pd,
X is the hydride anion ($H^-$) or methylide ($CH_3^-$),
a is 1 or 2 and
n is 0, 1 or 2.

In these alternative embodiments, the at least one N-aminoguanidinate-ligand is N,N'-bisdimethylamino-N''-dimethylguanidinate (bdmg).

In further specific embodiments, the metal complexes are of formula 4, wherein M is Ga, Zn or Fe, X is the hydride anion (H⁻) or methylide (CH₃⁻), a is 1 or 2 and n is 0, 1 or 2. In these embodiments with the metal complexes are of formula 4, the at least one N-aminoguanidinate-ligand is N,N'-bisdimethylamino-N''-dimethylguanidinate (bdmg). In some more specific embodiments, X is methylide, a and n are both 1 or 2.

In yet another specific embodiment, the metal complexes have the following formula 5

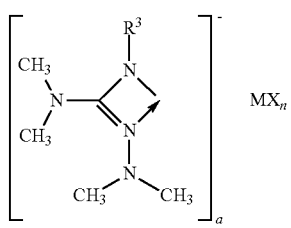

formula 5 wherein
M is La, Ce, Pr, Nd, Sm or Yb;
R³ is CH₃ or N(CH₃)₂;
X is the hydride anion (H⁻) or methylide (CH₃⁻);
a is 1, 2 or 3; and
n is 0, 1 or 2.

In yet another specific embodiment, the metal complexes have the following formula 6

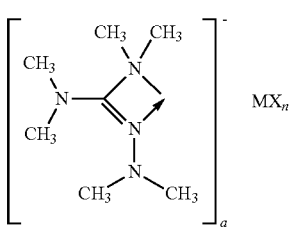

formula 6 wherein
M is Ce, Pr, Nd, Sm or Yb;
X is the hydride anion (H⁻) or methylide (CH₃⁻);
a is 1, 2 or 3; and
n is 0, 1 or 2.

In an even more specific embodiment, the metal complexes have the formula 6, wherein M is Ce, Pr, Nd, Sm or Yb, n is 0 and a is 3.

The present patent application also relates to a method for producing these new metal complexes.

The method comprises the steps of:
1) Preparing an N-aminoguanidine ligand;
2) Preparing a metal complex from the N-aminoguanidine ligand.

The preparation of an N-aminoguanidine ligand (step 1) comprises reacting a hydrazine with the general formula H₂N—NR$^x$R$^y$ with a compound selected from the group of thioureas and 1,1-dichloromethanamines. R$^x$ and R$^y$ of the formula H₂N—NR$^x$R$^y$ are preferably independently of each other hydrogen or a linear or branched alkyl radical having up to 4 carbon atoms.

The reaction of the hydrazine with the general formula H₂N—NR$^x$R$^y$ with a compound selected from the group of thioureas and 1,1-dichloromethanamines comprises mixing both components in a reaction solvent to form a ligand preparation mixture.

Preferably, the reaction of the hydrazine with the general formula H₂N—NR$^x$R$^y$ with a compound selected from the group of thioureas and 1,1-dichloromethanamines is carried out such that the compound selected from thioureas and 1,1-dichloromethanamines is mixed with the reaction solvent to form a ligand preparation pre-mixture. Preferably, the hydrazine compound is added subsequently to the ligand preparation pre-mixture to form the ligand preparation mixture. Preferably, the hydrazine compound is added slowly to the ligand preparation pre-mixture. More preferably, the hydrazine compound is added drop-wise. The described preferred order allows for a further increase of the yield of the prepared ligand. The ligand preparation pre-mixture and the ligand preparation mixture may contain further compounds.

Preferably, the reaction solvent of step 1) is selected from the group of aliphatic hydrocarbons, aromatic solvents, chlorinated solvents, ethereal solvents, alcohols and mixtures thereof. More preferably, the reaction solvent of step 1) is selected from the group of pentane, hexane, heptane, benzene, toluene, dichloromethane, chloroform, diethyl ether, tetrahydrofuran, methanol, ethanol, isopropanol and mixtures thereof. Even more preferably, the reaction solvent of step 1) is selected from dichloromethane, chloroform and tetrahydrofuran.

In a preferred version of the method R$^x$ or R$^y$ of the formula H₂N—NR$^x$R$^y$ are independently of each other hydrogen or a methyl group. In a further preferred version of the method both R$^x$ and R$^y$ are methyl groups.

The reaction of the hydrazine with the general formula H₂N—NR$^x$R$^y$ with a compound selected from the group of thioureas and 1,1-dichloromethanamines may further comprise an activation step. The activation step is preferably not conducted in case the hydrazine is reacted with a compound selected from the group of 1,1-dichloromethanamines.

In case the hydrazine is reacted with a compound selected from the group of thioureas step 1) preferably comprises the activation step. In these embodiments, the activation step preferably comprises an alkylation of the thio group of the compound selected from the group of thioureas. More preferably, the activation step comprises a methylation of the thio group of the compound selected from the group of thioureas.

In embodiments in which the reaction of the hydrazine with a compound selected from the group of thioureas comprises the activation step, the activation step is carried out before the ligand preparation pre-mixture and mixture is formed.

Preferably, the reaction time of the activation step is at least 1 hour, more preferably at least 2 hours and even more preferably at least 3 hours. If the reaction time is too short, the activated compound cannot be obtained with a high yield. Preferably, the reaction time the activation step does not exceed 4 days, more preferably 3 days, even more preferably 2 days. If the reaction time is too long, the probability of precipitation is increased. It is particularly preferred that the reaction time of the activation step is between 6 hours and 36 hours.

Preferably, the reaction temperature of the activation step is at least −80° C., more preferably −50° C., even more preferably −30° C. If the reaction temperature is too low, the reaction does not proceed fast enough. Preferably, the reaction temperature does not exceed 100° C., more preferably 80° C. even more preferably 60° C. If the reaction temperature is too high, unwanted side-reactions occur. It is particularly preferred that the reaction temperature is between −20° C. and 50° C.

The terms "thiourea" and "1,1-dichloromethanamine" are used according to the present patent application for such compounds that have a thiourea and 1,1-dichloromethanamine basic structure, respectively. Such compounds can have additional substituents such as alkyl radicals attached to the respective basic structure.

Preferably, the thiourea is selected from the group of dimethylthiourea, trimethylthiourea, diethylthiourea, triethylthiourea, dimethylethylthiourea and diethylmethylthiourea. More preferably, the thiourea is selected from the group of dimethylthiourea, trimethylthiourea and dimethylethylthiourea. Even more preferably, the thiourea is trimethylthiourea. Moreover, phosgene imminium salts are also suitable for the reaction with hydrazine.

Preferably, the 1,1-dichloromethanamine is selected from the group of 1,1-dichloromethanmethylamine, 1,1-dichloromethandimethylamine, 1,1-dichloromethanethylamine, 1,1-dichloromethandiethylamine and 1,1-dichloromethanmethylethylamine. More preferably, the 1,1-dichloromethanamine is selected from the group of 1,1-dichloromethanmethylamine, 1,1-dichloromethandimethylamine and 1,1-dichloromethanethylamine. Even more preferably, the 1,1-dichloromethanamine is 1,1-dichloromethandimethylamine; a suitable phosgene imminium salt is dichloromethylenedimethylimminium chloride. This compound has the formula

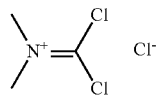

The preparation of a metal complex from the N-aminoguanidine ligand (step 2) of the method comprises the following reaction steps:
  a) optionally deprotonating the N-aminoguanidine ligand to form an N-aminoguanidinate-ligand;
  b) providing a metal complex preparation mixture, which comprises the N-aminoguanidine ligand or the N-aminoguanidinate ligand obtained from optional step a), at least one metal starting compound and a reaction solvent;
  c) incubating the obtained metal complex preparation mixture with optional stirring;
  d) evaporating the reaction solvent;
  e) optionally purifying the remaining reaction product, preferably by washing with a washing solvent.

Optionally, the N-aminoguanidine ligand is deprotonated in step a) to form an N-aminoguanidinate ligand, which is monoanionic according to the present patent application. The deprotonation of the aminoguanidine ligand (step a)) is preferably carried out by incubation of the aminoguanidine ligand with a base. Preferably, the base is selected from the group of potassium hexamethyl disilazide (KHMDS), lithium hexamethyl disilazide (LiHMDS), lithium diisopropylamide (LDA) and lithium tetramethylpiperidide (LiTMP). More preferably, the base is selected from KHMDS or LiHMDS. Even more preferably, the base is KHMDS.

Preferably, the reaction time of step a) is at least 1 minute, more preferably at least 2 minutes and even more preferably at least 5 minutes. If the reaction time is too short, the deprotonated ligand cannot be obtained with a high yield. Preferably, the reaction time of step a) does not exceed 5 hours, more preferably 4 hours, even more preferably 3 hours. If the reaction time is too long, the probability of precipitation is increased. It is particularly preferred that the reaction time of step a) is between 10 minutes and 1 hour.

Preferably, the reaction temperature of step a) is at least −80° C., more preferably −50° C., even more preferably −20° C. If the reaction temperature is too low, the reaction does not proceed fast enough. Preferably, the reaction temperature does not exceed 100° C., more preferably 80° C. even more preferably 60° C. If the reaction temperature is too high, unwanted side-reactions occur. It is particularly preferred that the reaction temperature is between 0° C. and 50° C.

In step b), the metal complex preparation mixture is formed, preferably by a single-step reaction. A single-step reaction is a reaction without necessitating intermediate isolation or intermediate purification steps.

The metal complex preparation mixture comprises the N-aminoguanidine-ligand or the N-aminoguanidinate-ligand obtained from step a), at least one metal starting compound and a reaction solvent.

The provision of the metal complex preparation mixture preferably comprises mixing the N-aminoguanidine-ligand or the N-aminoguanidinate-ligand obtained from step a) with at least one metal starting compound in a reaction solvent to form the metal complex preparation mixture. In embodiments in which the method comprises step a), the metal complex preparation mixture comprises the N-aminoguanidinate-ligand, at least one metal starting compound and a reaction solvent. In alternative embodiments in which the method does not comprise step a), the metal complex preparation mixture comprises at the N-aminoguanidine-ligand, at least one metal starting compound and a reaction solvent.

The mixing of the N-aminoguanidine-ligand or the N-aminoguanidinate-ligand obtained from step a) with at least one metal starting compound in a reaction solvent may be carried out such that the at least one metal starting compound is mixed with the reaction solvent to form a metal complex preparation pre-mixture. Preferably, the N-aminoguanidine-ligand or the N-aminoguanidinate-ligand obtained from step a) is added subsequently to the metal complex preparation pre-mixture for obtaining the metal complex preparation mixture. Preferably, the N-aminoguanidine-ligand or the N-aminoguanidinate-ligand obtained from step a) is added slowly to the metal complex preparation pre-mixture. More preferably, the N-aminoguanidine-ligand or the N-aminoguanidinate-ligand obtained from step a) is added drop-wise. The described preferred order allows for a further increase of the yield of the metal complexes. The metal complex preparation pre-mixture and the metal complex preparation mixture may contain further compounds.

In an alternative embodiment, the mixing of the N-aminoguanidine-ligand or the N-aminoguanidinate-ligand obtained from step a) with at least one metal starting compound in a reaction solvent may be carried out such that the N-aminoguanidine-ligand or the N-aminoguanidinate-ligand obtained from step a) is mixed with the reaction solvent to form a metal complex preparation pre-mixture. In such an embodiment, the at least one metal starting compound is added subsequently to the metal complex preparation pre-mixture for obtaining the metal complex preparation mixture. Preferably, the at least one metal starting compound is added slowly to the metal complex preparation pre-mixture. More preferably, the at least one metal starting compound is added drop-wise.

Suitable metal starting compounds are preferably selected from the group of metal hydrides, metal halides, metal alkylides, metal arylides, metal alkoxylates, metal alkylthiolates, metal alkylselenolates, metal nitrile complexes such as [$PdCl_2(CH_3CN)_2$] and metal amides. More preferably, metal starting compounds are selected from the group of metal hydrides, metal methylides, metal ethylides, metal methylates, metal ethylates, metal dimethylamides, metal diethylamides, metal methylethylamides, metal chlorides and metal bromides. More preferably, the metal starting compounds are selected from the group of metal hydrides, metal methylides, metal ethylides, metal dimethylamides and metal chlorides. Even more preferably, the metal starting compounds are selected from the group of metal hydrides, metal methylides and metal chlorides. In especially preferred embodiments a single type metal starting compound is used.

Preferably, the molar ratio of the N-aminoguanidine ligand or the N-aminoguanidinate ligand to the at least one metal starting compound is at least 0.1, more preferably at least 0.2 and even more preferably at least 0.4. If the molar ratio is too low, the inventive metal complexes cannot be obtained with a high yield. Preferably, the ratio does not exceed a value of 20, more preferably of 10 and even more preferably of 3. If the molar ratio is too high, the inventive metal complexes cannot be obtained with a high yield. It is particularly preferred that the molar ratio of the N-aminoguanidine ligand or the N-aminoguanidinate ligand to the at least one metal starting compound is between 0.45 and 2.5.

The metal complex preparation mixture comprises a reaction solvent. Preferably, the reaction solvent is an organic solvent selected from the group of aliphatic hydrocarbons, aromatic solvents, chlorinated solvents, ethereal solvents, alcohols or mixtures thereof. More preferably, the reaction solvent is selected from the group of pentane, hexane, heptane, benzene, toluene, dichloromethane, chloroform, diethyl ether, tetrahydrofuran, methanol, ethanol, isopropanol or mixtures thereof. Even more preferably, the reaction solvent is selected from hexane, toluene, diethyl ether and tetrahydrofuran.

Preferably, the reaction time of step c) is at least 10 minutes, more preferably at least 20 minutes and even more preferably at least 30 minutes. If the reaction time is too short, the inventive metal complexes cannot be obtained with a high yield. Preferably, the reaction time of step c) does not exceed 5 days, more preferably 4 days, even more preferably 3 days. If the reaction time is too long, the probability of precipitation is increased. It is particularly preferred that the reaction time of step c) is between 45 minutes and 48 hours.

Preferably, the reaction temperature of step c) is at least −180° C., more specifically −150° C., even more specifically −120° C. or −78° C. If the reaction temperature is too low, the reaction does not proceed fast enough. Preferably, the reaction temperature does not exceed 200° C., more specifically 80° C. even more specifically 60° C. If the reaction temperature is too high, unwanted side-reactions occur. Consequently, the reaction temperature is between −50° C. and 200° C., or −100° C. and 70° C., or −100° C. and 50° C.

Subsequent to reaction step c) the reaction solvent is separated by evaporation (step d)). Evaporation is preferably done at pressures of less than 10 mbar, more preferably less than 1 mbar, more preferably less than $10^{-3}$ mbar and even more preferably less than $10^{-3}$ mbar. If the pressure is too high, the evaporation rate is too low.

The remaining reaction product may be further purified (step e)). This is preferably done by washing the reaction product from step d) with a washing solvent. The washing solvent is preferably selected from the group of aliphatic alcohols and alkanes or mixtures thereof. More preferably, the washing solvent is selected from methanol, pentane and hexane or mixtures thereof. Even more preferably, the washing solvent is hexane. Further purification steps may be conducted.

Reaction steps 1) and 2) of the method of the present patent application are preferably carried out under an inert gas. In particular, the inert gas is selected from the group of nitrogen and argon. More specifically, the inert gas is nitrogen.

EXAMPLES

Abbreviations

Me: methyl, —CH$_3$

DCM: Dichloromethane

DEE: Diethyl ether

MHz: megahertz, $10^6$ s$^{-1}$

Figure 1:
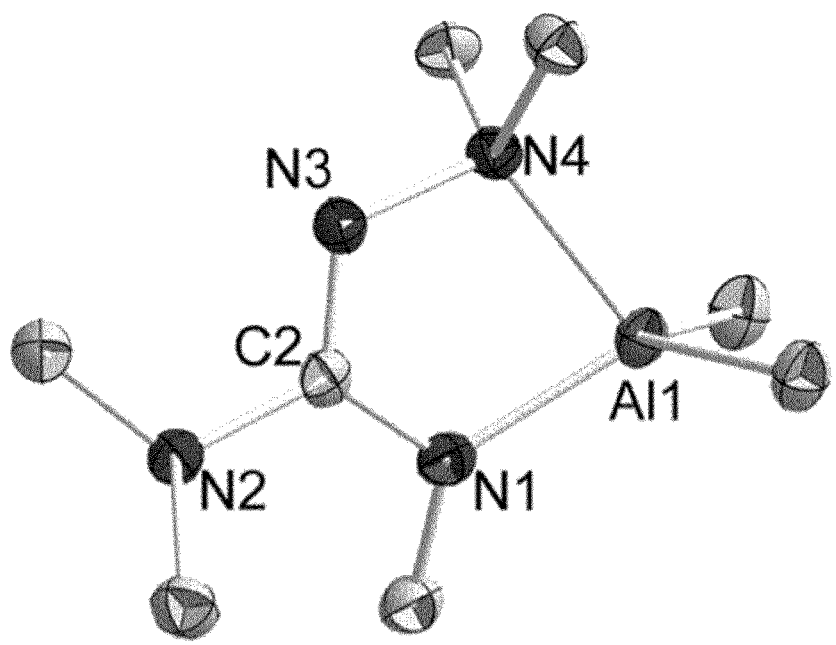
FIG. 1 shows an ORTEP plot of the crystal structure of Al(datg)Me$_2$ (example 4). Nitrogen atoms are labelled N1 to N4, respectively. The central carbon atom of the guanidine group is labelled C2. The aluminium atom is labelled Al1. The carbon atoms in the methyl groups are not labelled. Hydrogen atoms are not shown. All bonds are shown as stick representations.
Figure 2:
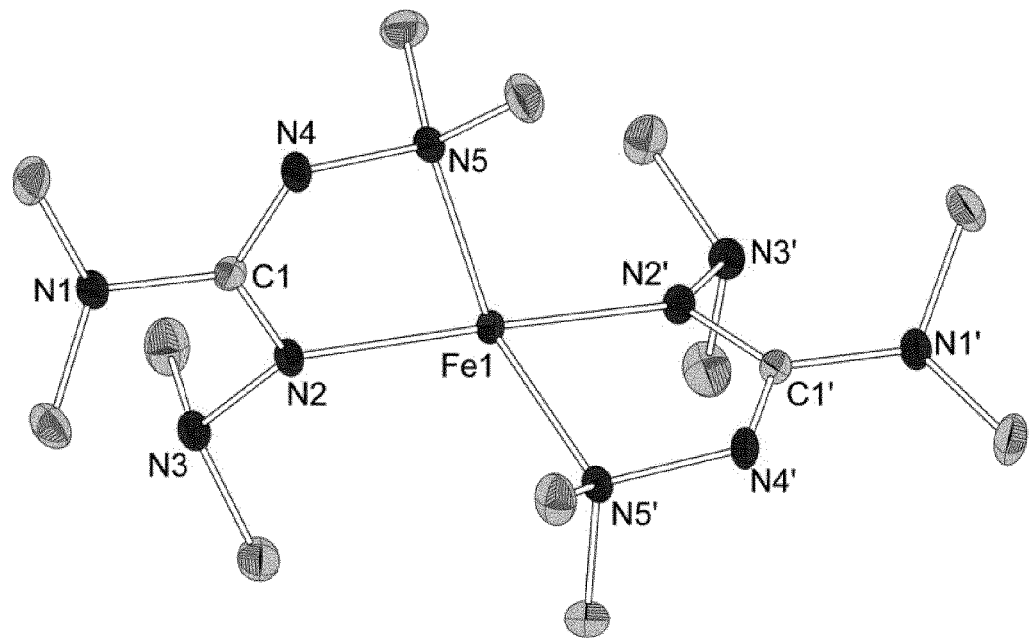
FIG. 2 shows an ORTEP plot of the crystal structure of Fe(bdmg)$_2$ (example 10). Nitrogen atoms are labelled N1 to N5 or N1' to N5', respectively. The central carbon atoms of the guanidine groups are labelled C1 and C1'. The iron atom is labelled Fe1. The carbon atoms in the methyl groups are not labelled. Hydrogen atoms are not shown. All bonds are shown as stick representations.
Figure 3:
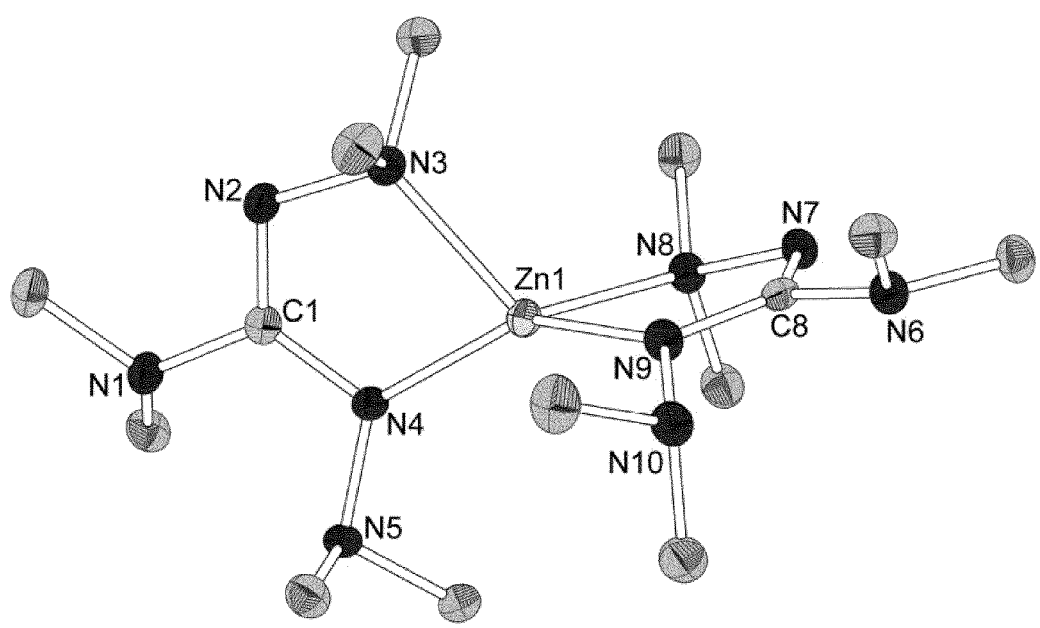
FIG. 3 shows an ORTEP plot of the crystal structure of Zn(bdmg)$_2$ (example 11). Nitrogen atoms are labelled N1 to N10, respectively. The central carbon atoms of the guanidine groups are labelled C1 and C8. The zinc atom is labelled Zn1. The carbon atoms in the methyl groups are not labelled. Hydrogen atoms are not shown. All bonds are shown as stick representations.
Figure 4:
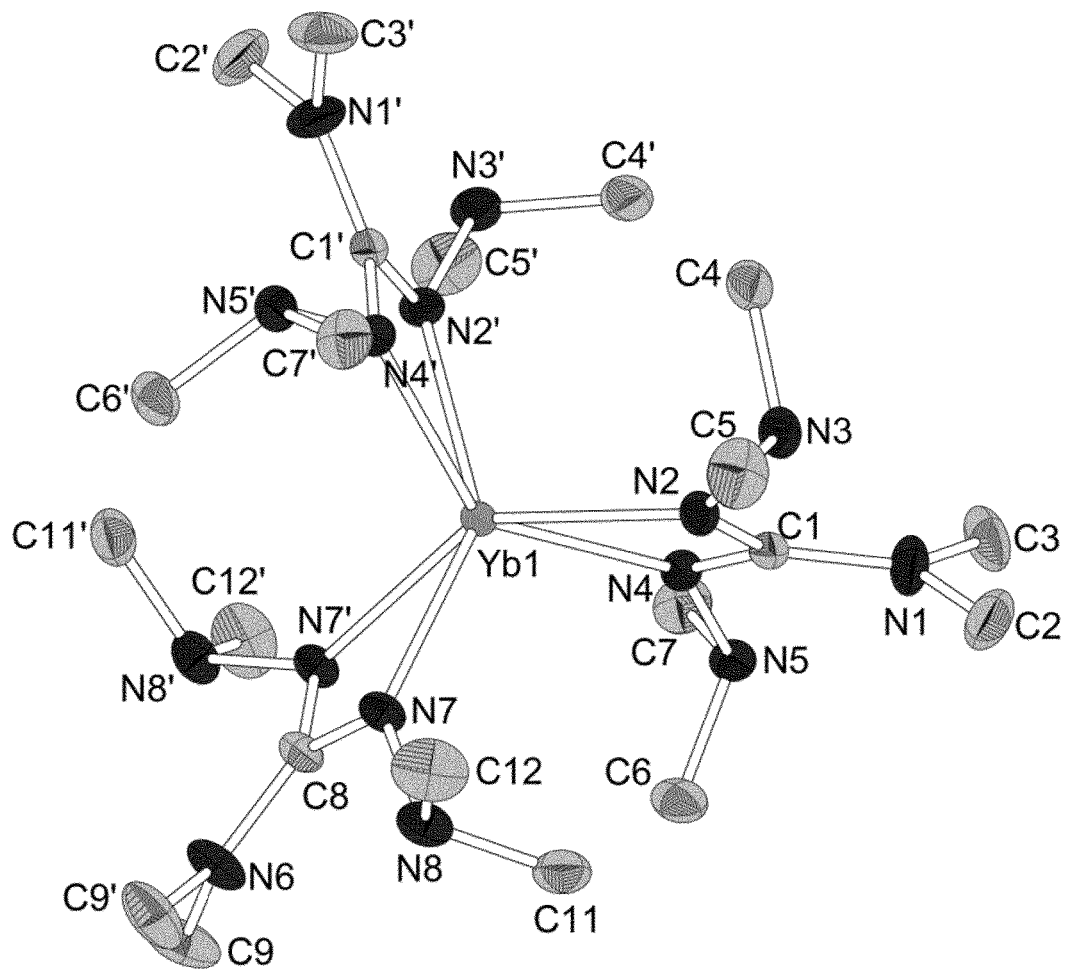
FIG. 4 shows an ORTEP plot of the crystal structure of Yb(bdmg)$_3$ (example 12). Nitrogen atoms are labelled N1 to N8 or N1' to N8', respectively. The central carbon atoms of the guanidine groups are labelled C1, C1' and C8. The ytterbium atom is labelled Yb1. The carbon atoms in the methyl groups are not labelled. Hydrogen atoms are not shown. All bonds are shown as stick representations.

MeCN: acetonitrile ppm: parts per million, unit of chemical shift in NMR spectroscopy THF: tetrahydrofuran TMS: tetramethylsilane For the multiplicities in the NMR spectra the abbreviations are as follows:
s: singlet
bs: broad singlet
d: doublet
Intensities in the IR spectra are abbreviated as follows:
w: weak
m: moderately strong
s: strong
b: broad General Remarks All syntheses have been performed under $N_2$ inert gas conditions using a common Schlenk line or an inert gas glovebox workstation (Braun). The nitrogen gas used was dried using columns filled with $P_4O_{10}$ resin. The vacuum-inert-gas-pipe was connected to a rotary vane pump (Vakuubrand).

The solvents used were dried by standard procedures (W. L. F. Armarego, D. D. Perrin, *Purification of laboratory chemicals*, 4. ed., Elsevier, Burlington, 1996) and stored in absorption columns over aluminium oxide/molecular sieve 3 Å/R3-11G-catalyst (BASF).

The chemical shift δ of the NMR spectra is specified in ppm relative to TMS as internal standard. Residual protons or respectively solvent signals of the respective deuterated solvent are used for calibration of the $^1$H- and $^{13}$C-NMR scales ($^1$H-NMR: $CDCl_3$: 7.26 ppm, $C_6D_6$: 7.16 ppm; $^{13}$C-NMR: $CDCl_3$: 77.16 ppm, $C_6D_6$: 128.06 ppm).

Buyable educts were purchased at the companies Sigma Aldrich, TCI Europe, Alfa Aesar and Merck. KHMDS (J. Åhman, P. Somfai, *Synth. Commun.* 1995, 25, 2301-2303) and dichloromethylethylendimethyl-ammoniumchloride (M. Vilkas, D. Qasmi, *Synth. Commun.* 1990, 20, 2769-2773) were prepared as described in the respective literature instructions.

Examples 1 and 2: Preparation of an N-Aminoguanidine Ligand

Example 1

Preparation of N-dimethylamino-N',N''-trimethyl-guanidine (Hdatg)

Trimethylthiourea (11.85 g, 100 mmol, 1.00 equivalent) was suspended in 20 ml DCM at 0° C. Methyl iodide (MeI) (6.40 ml, 103 mmol, 1.03 equivalents) was added drop-wise and the solution was slowly heated to room temperature (RT). After 24 hours the intermediate product was concentrated in vacuum. The clear, yellow and highly viscous oil crystallized slowly. MeI was dissolved with 10 ml THF. All other volatile components were removed in vacuum. The sulfonium salt obtained was dissolved in 8 ml MeCN. N,N-dimethylhydrazine (8.5 ml, 112 mmol, 1.12 equivalents) was added, the solution was stirred for 2 hours at 40° C. and subsequently for 15 minutes at RT. Methanethiol was removed with $N_2$. MeCN was removed in vacuum. The residues were washed with concentrated $KOH_{aq}$ and extracted with DCM. DCM was removed in vacuum and the product was distilled (35 mbar, 68° C.-73° C.). 7.64 g (53.0 mmol, 53%) of the clear product were obtained.

$^1$H-NMR (300 MHz, $C_6D_6$): δ=5.73 (s, 1H, NH), 2.55 (s, 6H, $NNMe_2$), 2.46 (s, 6H, $NMe_2$), 2.38 (d, 3H, J=5.7 Hz, NHMe).
$^{13}$C-NMR (75 MHz, $C_6D_6$): δ=164.9 ($C_q$), 48.8 ($NNMe_2$), 39.8 ($NMe_2$), 31.3 (NMe).

HR-MS (ESI): m/z calculated for $[M+H]^+$: 145.1448, found: 145.1448.
IR: $\tilde{v}$ ($cm^{-1}$)=2980 (w), 2948 (m), 2853 (m), 2817 (w), 2772 (w), 1640 (s), 1466 (w), 1449 (w), 1340 (w), 1254 (w), 1157 (m), 1016 (m), 959 (s), 899 (w), 682 (b), 594 (w), 447 (w).

Example 2

Preparation of N,N'-bis(dimethylamino)-N''-dimethylguanidine (Hbdmg)

N,N-dimethylhydrazine (0.47 ml, 6.16 mmol, 2.0 equivalents) and triethylamine (1.50 ml, 10.80 mmol, 3.5 equivalents) were slowly added drop-wise and under stirring to dichloromethylethylendimethyl-ammoniumchloride (500 mg, 3.08 mmol, 1.0 equivalent) in 5 ml THF at −10° C. After 1 hour the solution was slowly heated to RT. The occurring precipitate was removed by filtering and the volatile components were removed under reduced pressure. The product (517 mg, 2.98 mmol, 97%) was obtained as clear oil.

$^1$H-NMR (300 MHz, $CDCl_3$): δ=2.80 (s, 6H, $NMe_2$), 2.46 (s, 6H, $NNMe_2$), 2.33 (s, 6H, $NNMe_2$), 6.78 (s, 1H, NH).
$^{13}$C-NMR (75 MHz, $CDCl_3$): δ=162.1 ($C_q$), 48.2 ($NHMe_2$), 47.1 ($NNMe_2$), 38.9 ($NMe_2$).
HR-MS (ESI): m/z calculated for $[M+H]^+$: 174.1713, found: 174.1713.

Examples 3 to 9: Preparation of Metal Complexes from an N-Aminoguanidine Ligand

In the examples below, Examples 3 to 5 and 7 to 9 describe complexes with the ligand datg, Example 6 describes a complex with the ligand bdmg.

Example 3

Preparation of [Pd(datg)$_2$]

KHMDS (219 mg, 1.1 mmol, 2.2 equivalents) was dissolved in 5 ml toluene and Hdatg (159 mg, 1.1 mmol, 2.2 equivalents) was added drop-wise under stirring. The reaction mixture was stirred for 15 minutes. Subsequently, the solvent and H-HMDS were removed in vacuum. The Kdatg obtained was dissolved in 3 ml THF and was slowly added drop-wise to [PdCl$_2$(MeCN)$_2$] (200 mg, 0.77 mmol, 1.0 equivalent) in 3 ml THF. The solution was stirred 30 minutes at room temperature and subsequently 30 minutes at 40° C. KCl was removed by centrifugation and the solvent was removed from the orange supernatant in vacuum. The resulting orange-brown solid was washed with hexane and dried in vacuum. 87 mg (0.22 mmol, 29%) of the desired product were obtained as orange solid.

$^1$H-NMR (300 MHz, $C_6D_6$): δ=2.81 (s, 6H, PdNMe), 2.56 (s, 12H, $PdNMe_2$), 2.47 (s, 12H, $NMe_2$).
$^{13}$C-NMR (75 MHz, $C_6D_6$): δ=160.2 ($C_{quart}$), 53.9 (Pd-$NMe_2$), 41.9 ($NMe_2$), 39.4 (PdNMe).
HR-MS (APCI, MeCN): m/z calculated for $[M+H]^+$: 393.1706, found: 393.1701.
IR: $\tilde{v}$ ($cm^{-1}$)=2924 (b), 2862 (b), 1538 (s), 1482 (m), 1444 (m), 1362 (s), 1180 (w), 1117 (s), 1055 (w), 941 (m), 867 (w), 822 (m), 736 (w), 685 (w), 570 (m), 535 (m), 502 (m).

Example 4

Preparation of [Al(datg)Me$_2$]

Hdatg (415 mg, 2.88 mmol, 1.01 equivalents) in 5 ml toluene was slowly added drop-wise to trimethylaluminium (205 mg, 2.84 mmol, 1.00 equivalent) in 5 ml toluene at −78° C. After 1 hour the temperature was raised to 0° C. After 45 minutes it was stirred for 12 hours at RT. Subsequently, the solvent was removed in vacuum and a slightly yellow oil was obtained, which was crystallizing at around 10° C. The product was transferred by vaporization at 40° C. followed by condensation. A colourless crystalline solid (135 mg, 674 μmol, 24%) was obtained, which was easily melted by hand warmth.

$^1$H-NMR (300 MHz, $C_6D_6$): δ=2.72 (s, 3H, NMe), 2.51 (s, 6H, $NMe_2$), 2.19 (s, 6H, $NMe_2$), −0.45 (s, 6H, $AlMe_2$).

$^{13}$C-NMR (75 MHz, $C_6D_6$): δ=170.5 (CH), 48.7 ($NMe_2$), 40.6 ($NMe_2$), 31.8 (NMe), −11.2 ($AlMe_2$).

IR: $\tilde{\nu}$ ($cm^{-1}$)=3005, 2935, 2881, 2815, 2795, 1522, 1492, 1474, 1448, 1416, 1404, 1374, 1267, 1233, 1187, 1164, 1128, 1102, 1093, 1056, 999, 987, 935, 867, 823, 748, 719, 661, 589, 559, 491, 449, 413.

Melting point: no exact measurement, approximately >20° C.

Example 5

Preparation of [In(datg)$Me_2$]

Hdatg (290 mg, 2.01 mmol, 1.00 equivalent) in 3 ml toluene was slowly added drop-wise to trimethylindium (321 mg, 2.01 mmol, 1.00 equivalent) in 2.5 ml toluene at −78° C. After 45 minutes the temperature was raised to 0° C. After further 45 minutes it was stirred for 12 hours at RT. Subsequently, the solvent was removed in vacuum and a slightly pink oil was obtained. The product was transferred by vaporization at 40° C. followed by condensation. A colourless liquid (233 mg, 809 μmol, 40%) was obtained and identified as [In(datg)$Me_2$].

$^1$H-NMR (300 MHz, $C_6D_6$): δ=2.90 (d, 3H, J=1.1 Hz, NMe), 2.63 (d, 6H, J=1.5 Hz, $NMe_2$), 2.20 (s, 6H, $NMe_2$), −0.09 (d, 6H, J=1.7 Hz, $InMe_2$).

$^{13}$C-NMR (75 MHz, $C_6D_6$): δ=170.8 (CH), 50.0 ($NMe_2$), 41.5 ($NMe_2$), 35.0 (NMe), −8.7 ($InMe_2$).

IR: $\tilde{\nu}$ ($cm^{-1}$)=2991, 2915, 2862, 2805, 1615, 1590, 1524, 1483, 1444, 1414, 1401, 1360, 1267, 1224, 1182, 1147, 1120, 1054, 1006, 985, 941, 907, 860, 822, 690, 671, 555, 508, 481, 432.

Melting point: no exact measurement, <0° C.

Example 6

Preparation of [Ga(bdmg)$Me_2$]

Trimethylgallium (184 mg, 1.60 mmol, 1.00 equivalent) in 2 ml toluene at −78° C. was slowly added drop-wise to Hbdmg (275 mg, 1.60 mmol, 1.00 equivalent) in 3 ml toluene. After 1 hour the temperature was raised to 0° C. After further 45 minutes it was stirred for 36 hours at RT. Subsequently, the solvent was removed in vacuum and a slightly yellow oil (167 mg, 0.61 mmol, 38%) was obtained and identified as the desired product.

$^1$H-NMR (300 MHz, $CDCl_3$): δ=2.86 (s, 6H, $NMe_2$), 2.53 (s, 6H, $NNMe_2$), 2.48 (s, 6H, $NNMe_2$), −0.249 (s, 6H, $GaMe_2$).

$^{13}$C-NMR (75 MHz, $CDCl_3$): δ=166.1 ($C_{quart}$), 48.0 ($NNMe_2$), 47.8 ($NNMe_2$), 39.7 ($NMe_2$), −7.1 ($GaMe_2$).

Example 7

Preparation of [B(datg)$H_2$]

Lithium borohydride (150 mg, 6.8 mmol, 1 equivalent) was suspended in 10 ml THF. 2.2 ml of a 1 M $BCl_3$ solution in hexane (2.2 mmol, 0.3 equivalents) was slowly added drop-wise to the suspension at −78° C. The reaction mixture was stirred for 1 hour at RT. Subsequently, the mixture was cooled down to −78° C. and mixed with Hdatg (1.7 ml, 12.7 mmol, 1.8 equivalents). It was heated to RT and stirred overnight. The precipitate was removed from the reaction mixture using Celite™ and the clear filtrate was dried in high vacuum. 636 mg (4.1 mmol, 60%) of the product were obtained as colourless solid.

$^1$H-NMR ($CDCl_3$, 300 MHz): δ/ppm=2.68 (s, 6H, $CNMe_2$), 2.52 (s, 3H, NMe), 2.51 (s, 6H, $BNMe_2$).

$^{13}$C-NMR ($CDCl_3$, 75 MHz): Signal intensity too low due to poor solubility.

HR-MS(ESI): m/z calculated for $[M+H]^+$: 157.1619, found: 157.1621.

Example 8

Preparation of [Al(datg)$H_2$]

$LiAlH_4$ (164 mg, 4.3 mmol, 2.2 equivalents) was dissolved at −78° C. in 20 ml diethyl ether and trimethylamine hydrochloride (392 mg, 4.1 mmol, 2 equivalents) was added in portions. The reaction mixture was stirred for 1 hour at −78° C. Subsequently, it was heated to RT and stirred for another 12 hours at RT. Hdatg (0.26 ml, 2 mmol, 1 equivalent) was added drop-wise under constant stirring at 0° C. The mixture was heated to RT and stirred for 12 hours. The precipitate was removed using Celite™ and the clear filtrate was dried in high vacuum. The residual was suspended in 10 ml hexane and in 5 ml diethyl ether. The turbid solution was filtered and the solvent of the clear filtrate was removed in high vacuum. 165 mg (0.9 mmol, 48%) of a clear solid were obtained as product.

$^1$H-NMR ($CDCl_3$, 300 MHz): δ/ppm=4.02 (bs, 2H, $AlH_2$), 2.62 (s, 6H, $CNMe_2$), 2.47 (s, 9H, $NMe_2$, NMe).

$^{13}$C-NMR ($CDCl_3$, 75 MHz): Signal intensity too low due to poor solubility.

Example 9

Preparation of [Ga(datg)$H_2$]

Gallium trichloride (0.55 g, 2.6 mmol, 1 equivalent) was dissolved in 5 ml diethyl ether at −78° C. and added drop-wise to a suspension of lithium hydride (0.40 g, 50.3 mmol, 16 equivalents) in 5 ml diethyl ether cooled to −78° C. The reaction mixture was stirred for another 2 hours at −78° C. Subsequently, it was heated to RT and it was stirred overnight. The precipitate was removed by filtering and the clear filtrate was mixed at −78° C. with a solution of gallium trichloride (0.40 g, 2.3 mmol, 0.7 equivalents) in 4 ml diethyl ether also cooled to −78° C. The resulting suspension was heated to 0° C. and subsequently filtered. The filtrate was cooled to −78° C. and mixed with Hdatg (0.33 ml, 2.5 mmol, 0.8 equivalents). The resulting suspension was slowly heated to 0° C. and was stirred overnight. The reaction mixture was filtered using Celite™ and the clear filtrate was concentrated by evaporation in high vacuum at 0° C. 429 mg (1.9 mmol, 64%) of the product were obtained as white solid.

$^1$H-NMR ($CDCl_3$, 300 MHz): δ/ppm=5.2 (bs, 2H, $GaH_2$), 2.88 (s, 6H, $CNMe_2$), 2.67 (s, 9H, $NMe_2$, NMe).

$^{13}$C-NMR ($CDCl_3$, 75 MHz): δ/ppm=169.5 ($C_{quart.}$), 49.8 ($NNMe_2$), 40.2 ($NMe_2$), 33.4 (NMe).

Example 10

Synthesis of [Fe(bdmg)$_2$]

Hbdmg (300 mg, 1.73 mmol, 2.2 eq) was added drop wise to KHMDS (345 mg, 1.73 mmol, 2.2 eq) in toluene (10 mL) at room temperature. The mixture was stirred for 1 h during which a white precipitate formed, afterwards the volatile compounds were removed under reduced pressure. FeCl$_2$ (98.8 mg, 0.78 mmol, 1.0 eq) in toluene (15 mL) was added to the so prepared Kbdmg in toluene (10 mL). The solution was stirred for 48 h at 90° C. during which it turned yellow. The solvent was removed under reduced pressure, the dark yellow residue solved in hexane (25 mL), filtered through celite and the solvent again removed under reduced pressure. This led to the desired product in form of a dark yellow solid (136 mg, 0.34 mmol, 43%).

$^1$H-NMR (C$_6$D$_6$, 300 MHz): δ/ppm=−25.39 (s, 12H, C=NNMe$_2$), −25.18 (s, 12H, C—NNMe$_2$), −24.80 (s, 12H, CNMe$_2$).

IR: $\tilde{v}$ (cm$^{-1}$)=2960 (w), 2940 (w), 2746 (w), 1609 (w), 1507 (w), 1476 (w) 1363 (w), 1257 (s), 1173 (w), 1220 (w) 1143 (m), 1082 (s), 1064 (s), 1052 (s), 1011 (vs), 939 (w), 913 (w), 868 (m), 792 (vs), 732 (m), 664 (w), 558 (w), 523 (m), 488 (m).

Example 11

Synthesis of [Zn(bdmg)$_2$]

Hbdmg (2.2 g, 12.7 mmol, 2.0 eq) was added drop wise to [Zn(HMDS)$_2$] (2.44 g, 6.35 mmol, 1.0 eq) in toluene (10 mL) at room temperature. The solution was stirred for 4 h, afterwards the solvent was removed under reduced pressure. Sublimation of the white solid yielded 2.31 g (5.65 mmol, 89%) of the desired product.

$^1$H-NMR (C$_6$D$_6$, 300 MHz): δ/ppm=2.35 (s, 6H, C=NNMeMe), 2.37 (s, 6H, C=NNMeMe), 2.46 (s, 12H, C—NNMe$_2$), 2.96 (s, 12H, CNMe$_2$).

$^{13}$C-NMR (C$_6$D$_6$, 75 MHz): δ/ppm=41.1 (C—NNMe$_2$, CNMe$_2$), 50.2 (C=NNMe$_2$), 168.6 (C$_{quart}$).

HR-EI-MS: calc. for C$_{14}$H$_{36}$N$_{10}$Zn: 408.2416 m/z, found: 408.2429 m/z.

IR: $\tilde{v}$ (cm$^{-1}$)=2999 (m), 2930 (s), 2847 (m), 2804 (m), 2782 (m). 2759 (m), 1510 (vs), 1481 (vs), 1437 (vs), 1370 (vs), 1258 (m), 1222 (m), 1177 (m), 1143 (s), 1077 (m), 1003 (s), 941 (s), 914 (s), 872 (s), 801 (m), 731 (m), 669 (w), 558 (w), 521 (s), 449 (m), 424 (vs).

Example 12

Synthesis of [Yb(bdmg)$_3$]

Hbdmg (0.11 g, 0.65 mmol, 3.2 eq) was added to a solution of KHMDS (0.13 g, 0.65 mmol, 3.2 eq) in 5 mL THF. The mixture was stirred for 1 h, afterwards the volatile compounds were removed under reduced pressure. The residue was solved in 5 mL THF and a slurry of [YbCl$_3$(thf)$_3$] (0.1 g, 0.20 mmol, 1.0 eq) in THF (3 mL) was added at room temperature. The solution was stirred for 12 h, afterwards the solvent was removed under reduced pressure, toluene was added to the residue and KCl was filtered off. The solution was concentrated and the desired product was obtained as yellow crystals (62 mg, 0.09 mmol, 45%).

$^1$H-NMR (C$_6$D$_6$, 300 MHz): δ/ppm=2.24 (s, 6H, C=NN(CH$_3$)$_2$), 2.46 (s, 6H, C—NN(CH$_3$)$_2$), 2.83 (s, 6H, CN(CH$_3$)$_2$).

The invention claimed is:

1. Metal complex having at least one N-aminoguanidinate ligand, wherein this metal complex is of the following formula 1a or 1b

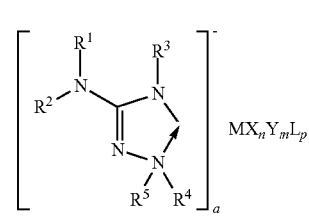

formula 1a

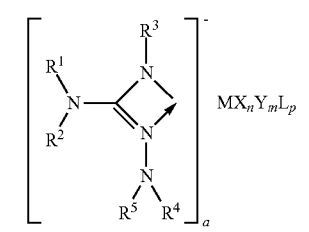

formula 1b wherein
- M is a metal selected from the groups 1 to 15 of the Periodic Table of the Elements (PTE), lanthanides or actinides,
- R$^1$ is hydrogen or a cyclic, linear or branched alkyl radical having up to 5 carbon atoms, NH$_2$, NH(CH$_3$), N(CH$_3$)$_2$, N(C$_2$H$_5$)$_2$ or N-pyrrolidinyl, or R$^1$ and R$^2$ together with the nitrogen atom they are bonded to form a pyrrolidinyl ring;
- R$^2$ is hydrogen or a cyclic, linear or branched alkyl radical having up to 5 carbon atoms, or R$^2$ and R$^1$ together with the nitrogen atom they are bonded to form a pyrrolidinyl ring;
- R$^3$ is hydrogen, CH$_3$, C$_2$H$_5$, NH$_2$, NH(CH$_3$), N(CH$_3$)$_2$, N(C$_2$H$_5$)$_2$ N-pyrrolidinyl or a SiMe$_3$ group,
- R$^4$ and R$^5$ independently of one another are hydrogen or a linear or branched alkyl radical having up to 4 carbon atoms, or R$^4$ and R$^5$ together with the nitrogen atom they are bonded to form a pyrrolidinyl ring;
- X is a monoanionic co-ligand selected from the hydride anion (H$^-$), from the group of the halides, from the group of the cyclic, linear or branched alkylides having up to 8 carbon atoms, from the group of substituted or unsubstituted arylides and heteroarylides having up to 10 C atoms, from the group of alkoxylato ligands, from the group of alkylthiolato or alkylselenolato ligands or from the group of secondary amido ligands,
- Y is a dianionic coligand selected from the oxo group [O]$^{2-}$, the sulfido group [S]$^{2-}$ or the imido group [NR$^6$]$^{2-}$, where R$^6$ is a cyclic, branched or linear alkyl having up to 8 carbon atoms or is a substituted or unsubstituted aryl having up to 20 carbon atoms,
- L is a neutral 2-electron donor ligand,
- a is an integer between 1 and 4 and
- n, m, and p each independently of one another are 0, 1, 2, 3 or 4.

2. Metal complex according to claim 1, wherein
- M is a metal selected from the groups 1 to 15 of the Periodic Table of the Elements (PTE), lanthanides or actinides, R¹ is hydrogen or a cyclic, linear or branched alkyl radical having up to 5 carbon atoms, NH₂, N(CH₃)₂ or N(C₂H₅)₂, R² is hydrogen or a cyclic, linear or branched alkyl radical having up to 5 carbon atoms, NH₂, N(CH₃)₂ or N(C₂H₅)₂, R³ is hydrogen, CH₃, C₂H₅, NH₂, N(CH₃)₂ or N(C₂H₅)₂, R⁴ and R⁵ independently of one another are hydrogen or a linear or branched alkyl radical having up to 4 carbon atoms, X is a monoanionic co-ligand selected from the hydride anion (H⁻), from the group of the halides, from the group of the cyclic, linear or branched alkylides having up to 8 carbon atoms, from the group of substituted or unsubstituted arylides and heteroarylides having up to 10 C atoms, from the group of alkoxylato ligands, from the group of alkylthiolato or alkylselenolato ligands or from the group of secondary amido ligands, Y is a dianionic coligand selected from the oxido group [O]²⁻ or the imido group [NR⁶]²⁻, where R⁶ is a cyclic, branched or linear alkyl having up to 8 carbon atoms or is a substituted or unsubstituted aryl having up to 20 carbon atoms, L is a neutral 2-electron donor ligand, a is an integer between 1 and 4 and n, m, and p each independently of one another are 0, 1, 2, 3 or 4.

3. Metal complex according to claim 1, wherein
R¹ is hydrogen or a cyclic, linear or branched alkyl radical having up to 5 carbon atoms,
R² is hydrogen or a cyclic, linear or branched alkyl radical having up to 5 carbon atoms,
R³ is hydrogen, CH₃, C₂H₅, NH₂, N(CH₃)₂ or N(C₂H₅)₂,
R⁴ and R⁵ are independently of one another hydrogen or a linear or branched alkyl radical having up to 3 carbon atoms,
X is the hydride anion (H⁻), methylide (CH₃⁻), ethylide (C₂H₅⁻), isopropylide (iso-C₃H₇⁻), tert-butylide (tert-C₄H₉⁻), the phenylide anion (C₆H₅⁻), the ortho-, meta-, or para-tolylide anion [C₆H₄(CH₃)]⁻, the thiophen-2-ylide anion (C₄H₃S⁻), methylato (MeO⁻), ethylato (EtO⁻), tert-butylato (tert-BuO⁻), MeS⁻, MeSe⁻, (tert-Bu)S⁻, (tert-Bu)Se⁻, dimethylamido (NMe₂⁻), diethylamido (NEt₂⁻), methylethylamido (NMeEt⁻), N-pyrrolidido [NC₄H₈]⁻, chloride (Cl⁻) or bromide (Br⁻),
Y is the oxo group [O]²⁻ or the imido group [NR⁶]²⁻, where R⁶ is a cyclic, branched or linear alkyl having up to 6 C atoms or is a substituted or unsubstituted aryl having up to 12 C atoms.

4. Metal complex according to claim 1, wherein
R¹ is hydrogen or a linear or branched alkyl radical having up to 4 carbon atoms,
R² is hydrogen or a linear or branched alkyl radical having up to 4 carbon atoms,
R³ is hydrogen, CH₃, C₂H₅, NH₂, N(CH₃)₂ or N(C₂H₅)₂,
R⁴ and R⁵ independently of one another are hydrogen, CH₃ or C₂H₅,
X is the hydride anion (H⁻), methylide (CH₃⁻), ethylide (C₂H₅⁻), the phenylide anion (C₆H₅⁻), the ortho-, meta-, or para-tolylide anion [C₆H₄(CH₃)]⁻, methylato (MeO⁻), ethylato (EtO⁻), MeS⁻, MeSe⁻, dimethylamido (NMe₂⁻), diethylamido (NEt₂⁻), methylethylamido (NMeEt⁻), chloride (Cl⁻) or bromide (Br⁻),
Y is the oxo group [O]²⁻ or the imido group [NR⁶]²⁻, where R⁶ is a branched or linear alkyl having up to 5 C atoms or is a substituted or unsubstituted aryl having up to 8 C atoms.

5. Metal complex according to claim 1, wherein
R¹ is hydrogen or a linear or branched alkyl radical having up to 3 carbon atoms,
R² is hydrogen or a linear or branched alkyl radical having up to 3 carbon atoms,
R³ is CH₃, C₂H₅, N(CH₃)₂ or N(C₂H₅)₂,
R⁴ and R⁵ independently of one another are CH₃ or C₂H₅,
X is the hydride anion (H⁻), methylide (CH₃⁻), ethylide (C₂H₅⁻), the phenylide anion (C₆H₅⁻), the ortho-, meta-, or para-tolylide anion [C₆H₄(CH₃)]⁻, methylato (MeO⁻), MeS⁻, dimethylamido (NMe₂⁻), diethylamido (NEt₂⁻) or chloride (Cl⁻),
Y is the imido group [NR⁶]²⁻, where R⁶ is a linear or branched alkyl having up to 4 C atoms.

6. Metal complex according to claim 1, wherein
R¹ and R² are both, independently of one another, a linear alkyl radical having up to 3 carbon atoms,
R³ is CH₃, C₂H₅ or N(CH₃)₂,
R⁴ and R⁵ independently of one another are CH₃ or C₂H₅,
X is a hydride anion (H⁻), methylide (CH₃⁻), ethylide (C₂H₅⁻), isopropylide (iso-C₃H₇⁻),
Y is the imido group [NᵗBu]²⁻.

7. Metal complex according to claim 1, having the formula 2

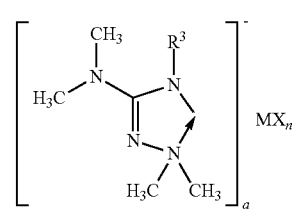

formula 2 wherein
M is B, Al, Ga, In, Fe, Zn or Pd,
R³ is CH₃ or N(CH₃)₂,
X is the hydride anion (H⁻) or methylide (CH₃⁻),
a is 1 or 2 and
n is 0, 1 or 2.

8. Metal complex according to claim 1, wherein the metal complexes have the following formula 3

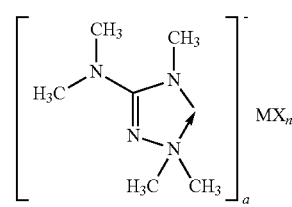

formula 3 wherein
M is B, Al, Ga, In, Zn, Fe or Pd,
X is the hydride anion (H⁻) or methylide (CH₃⁻),
a is 1 or 2 and
n is 0, 1 or 2.

9. Metal complex according to claim 8, wherein the N-aminoguanidinate-ligand is N-dimethylamino-N',N"-trimethylguanidinate (datg).

10. Metal complex according to claim 8, wherein M is B, Al, Ga, In or Pd.

11. Metal complex according to claim 1, wherein the metal complexes have the following formula 4

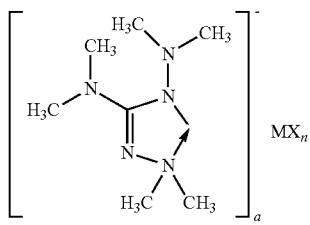

formula 4 wherein
M is B, Al, Ga, In, Zn, Fe or Pd,
X is the hydride anion (H⁻) or methylide ($CH_3^-$),
a is 1 or 2 and
n is 0, 1 or 2.

12. Metal complex according to claim 11, wherein the N-aminoguanidinate-ligand is N,N'-bisdimethylamino-N"-dimethylguanidinate (bdmg).

13. Metal complex according to claim 11, wherein M is Ga, Zn or Fe.

14. Metal complex according to claim 11, wherein X is methylide, a and n are both 1 or 2.

15. Metal complex according to claim 1, wherein the metal complexes have the following formula 5

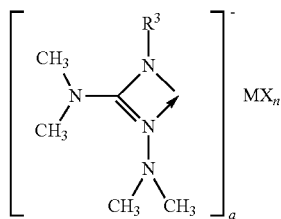

formula 5 wherein
M is La, Ce, Pr, Nd, Sm or Yb;
$R^3$ is $CH_3$ or $N(CH_3)_2$;
X is the hydride anion (H⁺) or methylide ($CH_3^-$);
a is 1, 2 or 3; and
n is 0, 1 or 2.

16. Metal complex according to claim 1, wherein the metal complexes have the following formula 6

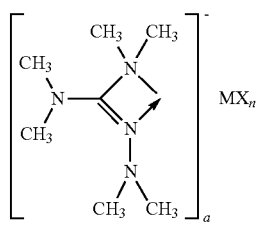

formula 6 wherein
M is Ce, Pr, Nd, Sm or Yb;
X is the hydride anion (H⁻) or methylide ($CH_3^-$);
a is 1, 2 or 3; and
n is 0, 1 or 2.

17. Metal complex according to claim 16, wherein M is Ce, Pr, Nd, Sm or Yb, n is 0 and a is 3.

18. Metal complex according to claim 1, wherein L is selected from pyridine, dioxane, $NH_3$, THF, CO, an alkylphosphine or an arylphosphine.

19. Metal complex according to claim 1, wherein L is selected from pyridine, $NH_3$, CO, $PMe_3$, $PCy_3$ and $PPh_3$.

20. Metal complex according to claim 1, wherein L is selected from $NH_3$ and CO.

21. Metal complex according to claim 1, wherein M is selected from the group of boron (B), aluminum (Al), gallium (Ga), indium (In), silicon (Si), germanium (Ge), tin (Sn), arsenic (As), antimony (Sb), titanium (Ti), zirconium (Zr), hafnium (Hf), chromium (Cr), manganese (Mn), iron (Fe), cobalt (Co), nickel (Ni), copper (Cu), zinc (Zn), ruthenium (Ru), rhodium (Rh), palladium (Pd) and platinum (Pt).

22. Metal complex according to claim 1, wherein M is selected from the group of boron (B), aluminum (Al), gallium (Ga), indium (In) and palladium (Pd).

23. Process for preparing the metal complex according to claim 1 comprising:
   a) optionally deprotonating the N-aminoguanidine ligand to an N-aminoguanidinate-ligand;
   b) providing a metal complex preparation mixture having the N-aminoguanidine ligand or the N-aminoguanidinate ligand obtained from optional step a), at least one metal starting compound and a reaction solvent;
   c) incubating the obtained metal complex preparation mixture with optional stirring;
   d) evaporating the reaction solvent;
   e) optionally purifying the reaction product of step d), preferably by washing with a washing solvent.

24. Process according to claim 23, wherein the reaction solvent is selected from pentane, hexane, heptane, benzene, toluene, dichloromethane, chloroform, diethyl ether, tetrahydrofuran, methanol, ethanol, isopropanol and mixtures thereof.

25. In a thin layer process involving a substrate coating step wherein the improvement comprises the metal complex according to claim 1 as a precursor.

26. The method according to claim 25, wherein the thin-film process is selected from the group of CVD processes, MO-CVD processes and ALD processes.

27. In a catalytic process for olefin hydroamination or olefinic polymerization wherein the improvement comprises the complex of claim 1 as the catalyst.

* * * * *